United States Patent [19]
Pasquereau et al.

[11] Patent Number: 6,134,942
[45] Date of Patent: Oct. 24, 2000

[54] SYSTEM FOR SAMPLING SPECIFIC POLLUTANTS CONTAINED IN DILUTED EXHAUST GASES FROM THERMAL ENGINES

[75] Inventors: Michel Pasquereau, Sartrouville; Jean-François Papagni, Saint Rémy les Chevreuses; Richard Levesque, Suresnes; Jean-Pierre Dumas, Sartrouville; Xavier Montagne, Rueil-Malmaison, all of France

[73] Assignee: Institut Francais du Petrole, Cedex, France

[21] Appl. No.: 09/337,261

[22] Filed: Jun. 22, 1999

[30] Foreign Application Priority Data

Jun. 26, 1998 [FR] France ..................... 98/08198

[51] Int. Cl.[7] .................................................. G01N 1/00
[52] U.S. Cl. ................................................. 73/23.31
[58] Field of Search .............................. 73/23.31, 23.32, 73/118.1, 863.03, 863.31, 863.32, 863.34, 864.73

[56] References Cited

U.S. PATENT DOCUMENTS

| | | |
|---|---|---|
| 3,406,562 | 10/1968 | Perna, Jr. et al. . |
| 4,758,521 | 7/1988 | Lushbaugh et al. ................ 436/128 |
| 4,759,210 | 7/1988 | Wohltjen .............................. 73/23 |
| 5,279,146 | 1/1994 | Asano et al. ........................ 73/28.04 |
| 5,498,279 | 3/1996 | Klemp . |
| 5,599,357 | 2/1997 | Lepper . |

FOREIGN PATENT DOCUMENTS

| | | |
|---|---|---|
| 0255856 | 2/1988 | European Pat. Off. . |
| 19607574 | 9/1997 | Germany . |

OTHER PUBLICATIONS

Patent Abstracts of Japan, vol. 012, No. 390 (P–772), Oct. 18, 1988 & JP 63 132161A (Agency of Ind. Science & Technol; Others: 01), Jun. 4, 1988 (Abstract).

Patent Abstracts of Japan, vol. 018, No. 250 (P–1736), May 12, 1994 & JP 06 34500 A (Honda Motor Co. Ltd.), Feb. 8, 1994 (Abstract).

Patent Abstracts of Japan, vol. 016, No. 006 (C–0900), Jan. 9, 1992 & JP 03 232516 A (Nissan Motor Co. Ltd.), Oct. 16, 1991 (Abstract).

*Primary Examiner*—Robert Raevis
*Attorney, Agent, or Firm*—Antonelli, Terry, Stout & Kraus, LLP

[57] ABSTRACT

The present invention is a system for specific pollutants contained in diluted exhaust gases from thermal combustion engines, comprising a first module (1) which samples aldehyde and ketone emissions and a second module (2) which samples hydrocarbon emissions. The system according to the invention further comprises a control which coordinates the sampling(s) with predetermined working phases of the thermal engine. The first module (1) comprises a circuit (3) for trapping the aldehydes and the ketones contained in the diluted exhaust gases and a dilution air sampling circuit (4).

20 Claims, 2 Drawing Sheets

SYSTEM FOR SAMPLING SPECIFIC POLLUTANTS CONTAINED IN DILUTED EXHAUST GASES FROM THERMAL ENGINES

BACKGROUND OF THE INVENTION

1. Field of the Invention

The present invention relates to the field of sampling gaseous fluids such as exhaust gases from thermal combustion engines in order to analyse them.

More precisely, the present invention relates to the sampling of gaseous fluids containing aldehydes and ketones, as well as hydrocarbons.

According to the invention, these two sampling methods can be carried out simultaneously or not, according to a selected analytic objective.

2. Description of the Prior Art

To date, most analysis laboratories performing individual aldehyde, ketone and hydrocarbon measurements in the exhaust gases of motor vehicles on chassis dynamometers work with their own measuring equipment, without any interactive connection between these various elements, i.e. without a really reliable, accurate and reproducible sampling protocol.

As regards aldehyde and ketone emissions, dinitrophenylhydrazine-grafted silica cartridges for sampling and chemically deriving these chemical species to hydrazone compounds are currently the most commonly used ones. Each cartridge must afterwards be subjected to a treatment in the analysis laboratory in order to dissolve these compounds in a solvent (acetonitrile). This sampling technique has the advantage of being effective, easy to use and it offers possibilities of medium-term storage of the samples. The hydrazone derivatives are then separated by injecting an aliquot of this solution into a HPLC (High-Performance Liquid Chromatography) unit and detected individually by UV (ultraviolet) absorption.

There is no compact commercial equipment using such cartridges and allowing the carrying out of the necessary stages of a sampling protocol such as control, monitoring and recording of the sampling parameters required for reliable and accurate quantification of the aldehyde and ketone emissions.

Concerning individual C1–C13 hydrocarbon emissions, and in order to have standard sampling conditions similar to those under which sampling of conventional pollutants (CO, total HC, $NO_x$) is carried out, Tedlar (chemically inert and plasticizer-free polyvinyl chloride film) storage bags are commonly used. These bags are generally installed in parallel with existing equipments in order to provide a certain representativeness of the diluted effluent supplied during the working cycle.

Other known methods transfer, after the tests, the gases collected in the sampling bags to smaller bags (10 to 20 litres) in order to convey them more readily to the analysis laboratory. A small volume is then injected into a gas chromatography unit according to particular analytic protocols (injection by calibrated loop, reconcentration of the sample on solid supports, . . . ). Sometimes, the gaseous effluents discharged by a diesel vehicle are not filtered, which pollutes the bags for good. In other known cases, filtering is such that hydrocarbon retention can lead to hydrocarbon-containing compound losses, notably those lower than C13.

There is no known equipment for sampling specific pollutants such as aldehydes, ketones, hydrocarbons, allowing sampling according to standard working cycles.

SUMMARY OF THE INVENTION

The invention has the following benefits:

It notably allows the use of known cartridges, fast and sealed setting in a suitable sampling support eliminating any external pollution, simple programming of the sampling parameters, and complete sampling automaticity when orders to start trapping of the effluents according to the working phase of the vehicle are given. Furthermore, the present invention allows permanent control of the sampling conditions during the working cycle (flow rates, temperatures, trapping time).

An advantageous use of the invention relates to sampling of exhaust gases of motor vehicles tested on chassis dynamometers during standard driving cycles. The present invention is designed to ensure automatically, during a predetermined driving cycle, several samplings associated with precise working phases of the vehicle.

The present invention allows modular, automated and interactive sampling of the gases discharged by a thermal engine in operation.

The present invention is a system which samples specific pollutants contained in diluted exhaust gases from thermal combustion engines, comprising a first module which samples aldehyde and ketone emissions and a second module which samples hydrocarbon emissions.

According to the invention, the system further comprises a means which coordinates the sampling(s) with predetermined working phases of the thermal engine.

In particular, the means comprises:

a circuit which traps the aldehydes and ketones contained in the diluted exhaust gases, comprising a gas passage simulation channel arranged parallel to at least one diluted gas sampling channel, these channels having a common inlet for the diluted gases and a common outlet connected to a line comprising a filtering element, a mass flow regulator and a pump arranged in series, and a dilution air sampling circuit comprising a gas passage simulation channel arranged parallel to at least one dilution air sampling channel, these channels having a common inlet for the dilution air and a common outlet connected to a line comprising a filtering element, a mass flow regulator and a pump arranged in series.

The first module can also comprise a drain circuit which cleans the circuits through which the diluted gases and the dilution air have flowed before entering the sampling module itself.

The aldehyde and ketone trapping circuit thus comprises at least one sampling cartridge placed in a sampling channel.

A solenoid valve can be placed downstream from each sampling cartridge, allowing either passage of the gases downstream or closing of the corresponding channel.

More precisely, the drain circuit comprises a general inlet for the drain gas and two parallel channels, one associated with the diluted exhaust gas trapping circuit, the other with the dilution air trapping circuit, both channels opening at one end into the general drain gas inlet and, at the other end, into either the diluted gas inlet or the dilution air inlet.

Each channel of the drain circuit advantageously comprises a solenoid valve situated close to the general drain gas inlet, allowing stopping circulation through the channel, and an element which fixes the flow rate of the drain gas in the channel.

According to the invention, the second sampling module which samples hydrocarbons comprises:

at least one general diluted exhaust gas inlet, at least a first channel equipped with a sampling bag, and another channel parallel to the first channel and allowing circulation of the gases outside said sampling bag, a selective orienting means which sends the exhaust gases to one of the channels, a general dilution air inlet, at least one channel equipped with a sampling bag and another channel allowing circulation of the dilution air outside the sampling bag, a selective orienting means which sends the dilution air to one of the channels.

Furthermore, a second treating means can comprise a circuit which drains at least one sampling bag from the gas it contains by means of draining/filling cycles.

More precisely, the drain circuit comprises a general drain gas inlet, a first solenoid valve connected to a pump, a second solenoid valve, an outlet and a link circuit for connection with the parallel channels.

In particular, the first solenoid valve is connected to the general inlet, to the pump and to the link circuit connected with the parallel channels.

Furthermore, the second solenoid valve is connected to the general outlet, to the pump and to the link circuit connected with the parallel channels.

The drain circuit further comprises a filter placed between the second solenoid valve and the parallel channels associated with the bags, the filter purifying air during the gas filling cycles.

The exhaust gas orienting means specifically comprises a solenoid valve placed on the gas circulation channel, a solenoid valve on the (or each) channel equipped with a sampling bag and a solenoid valve upstream from said parallel channels.

Furthermore, the dilution air orienting means comprises a solenoid valve placed on the air circulation channel, a solenoid valve on the (or each) channel equipped with a sampling bag and a solenoid valve upstream from said parallel channels.

According to a particular feature of the invention, the second hydrocarbon sampling module comprises two parallel channels proximate the general diluted gas inlet, one for the gases from diesel engines and the other for the gases from spark-ignition engines.

The diesel exhaust gas channel comprises a heated filter and an element which fixes the mass flow rate of the gas to be sampled, whereas the other channel comprises an element which fixes the mass flow rate of the gas to be sampled and a contaminant filter.

Furthermore, the system comprises, upstream from the parallel channels for sampling the diluted gases, a pump and a flowmeter.

Besides, the dilution air supply line comprises, upstream from the parallel channels, a filter, a pump and an adjustable flowmeter.

BRIEF DESCRIPTION OF THE DRAWINGS

Other features, advantages and details of the invention will be clear from reading the description hereafter, given by way of non limitative example, with reference to the accompanying drawings wherein.

DETAILED DESCRIPTION OF THE INVENTION

Figure 1:
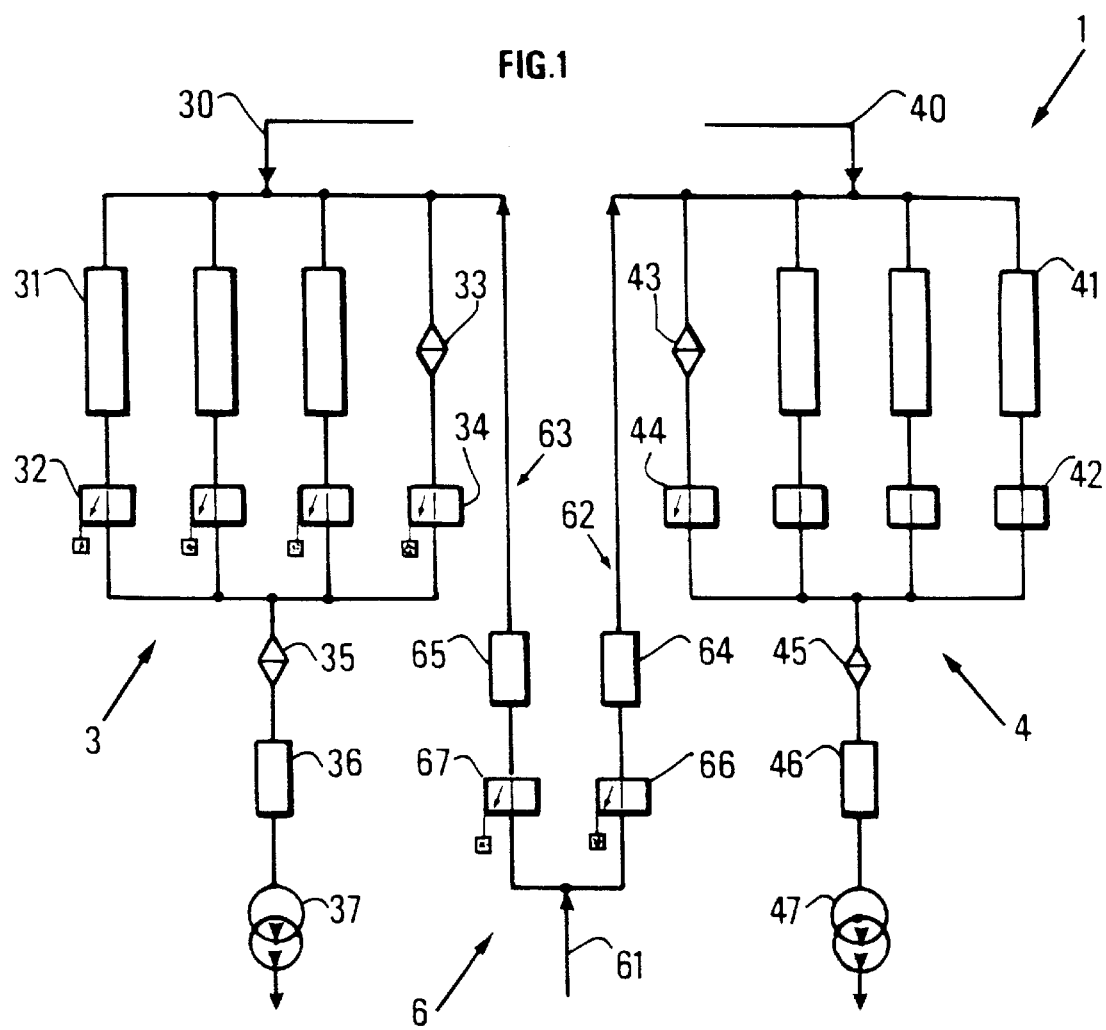
FIG. 1 is a diagram of the aldehyde and ketone sampling circuit.

FIG. 1 is a schematic of the aldehyde and ketone sampling module 1 according to the invention.

Overall the module comprises an aldehyde and ketone trapping circuit 3 having a general inlet 30 for the diluted gases that divides into several parallel channels: some comprise an aldehyde and ketone sampling device 31 (such as a Sep Pak Silica Waters cartridge for example), and a solenoid valve 32 for stopping the flow in each channel to order; another parallel channel which simulates the passage of the gases in the other channels and it comprises a filter 33 and a solenoid valve 34.

All these parallel channels have a common outlet on a single channel that can comprise a filter 35, a mass flow regulator 36 and a pump 37 arranged in series.

The first module 1 comprises a second general inlet 40 of a circuit 4 for sampling the dilution air used for diluting the gases.

Circuit 4 is overall organized like circuit 3, i.e. it comprises several parallel channels having a common general inlet 40. Several channels (three in this case) sample the dilution air, with a cartridge 41 and an associated solenoid valve 42, downstream from cartridge 41. Another channel simulates the passage of the gases in the sampling channels; this channel generally comprises a filter 43 in series with a solenoid valve 44. This channel circulates the diluted gases when it is not necessary to circulate them in the sampling channels themselves. Control of the various solenoid valves allows this selective distribution.

Any means known in the art can be used without departing from the scope of the invention to obtain this selective orientation (or distribution) of the gases. A multiway solenoid valve can be used for example.

The common outlet (bearing no reference number) of the parallel channels is connected to the inlet of a single channel preferably comprising a filter 45, a mass flow regulator 46 and a pump 47.

Sampling module 1 thus ensures sampling of the dilution air and of the diluted gases, which allows later determination of the composition of the non-diluted gases.

In addition, module 1 can comprise a drain circuit 6 that allows, once all the samplings are completed in module 1, countercurrent draining of the diluted gas and dilution air inlets.

A drain gas, nitrogen for example, is fed into a general inlet 61 that divides into two lines 62, 63; 62 opens onto dilution air inlet 40 whereas second line 63 opens onto general diluted gas inlet 30.

Each line 62, 63 comprises a solenoid valve 66, 67 and a means 64, 65 which fixes the flow rate of the drain gas; this means can be a capillary for example.

The dilution air and the diluted gases are preferably heated prior to entering the first module, by means of heating sticks for example.

Figure 2:
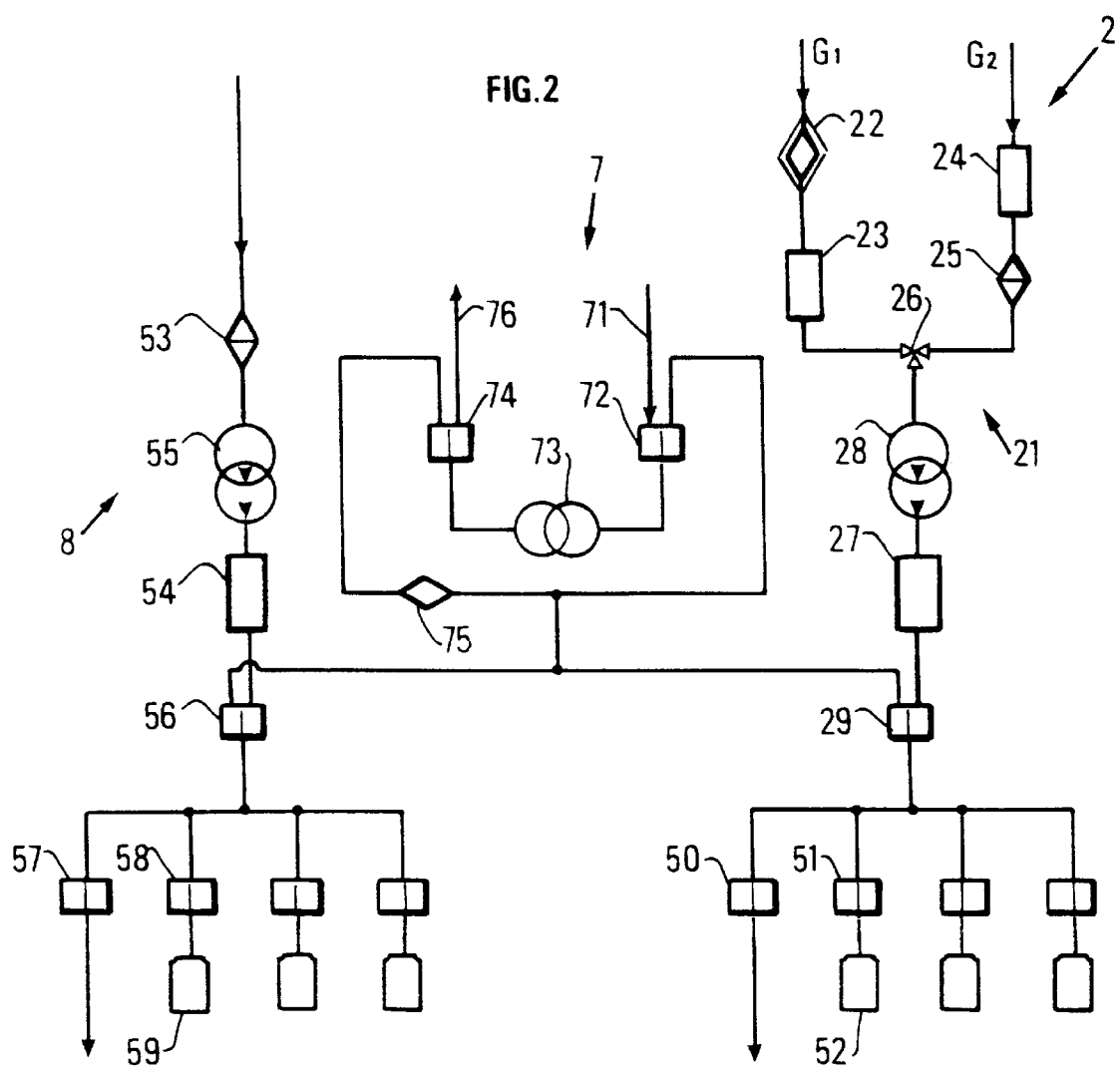
FIG. 2 is a diagram of the hydrocarbon sampling circuit.

FIG. 2 is a schematic of the main elements of hydrocarbon sampling module 2 that comprises a first assembly 21 for the diluted gases and a second assembly 8 for the dilution air. In addition, a third optional assembly 7 can be provided for draining the elements filled with gas.

More precisely, assembly 21 comprises at least one general inlet for the diluted gases. According to the embodiment of FIG. 2, there are two distinct inlets; one, G1, for exhaust gases from diesel engines and the other, G2, for exhaust gases from gasoline engines. Of course, this is entirely optional but it allows for the best treat of type of exhaust gas.

In this particular context, the gases from G1 flow through a heated filter holder 22, then through a calibrated port 23; heating prevents hydrocarbon retention; the gases from G2 first flow through a calibrated port 24, then through a filter 25 which retains the bigger impurities (clusters) possibly contained in the exhaust gases.

The two parallel channels G1, G2 join at valve 26 at the end of a transfer channel equipped here with a pump 28, a flowmeter 27 and a solenoid valve 29.

The transfer channel ends at a common inlet for several parallel channels: three parallel channels are provided here for sampling the hydrocarbons of the diluted gas; a fourth channel is also provided for gas circulation before sampling. The gas circulation channel comprises a solenoid valve 50 for adjusting the flow rate before sampling. The three parallel channels are each equipped with a solenoid valve 51 and a bag 52 for collecting the gases.

The number of channels equipped with sampling bags 52 is not necessarily three. A single channel or more can be provided without departing from the scope of the invention.

Furthermore, solenoid valves 29, 50 and 51, that appear in the embodiment of the invention illustrated by FIG. 2, can be replaced by any other means known in the art without departing from the scope of the invention, for selective distribution and orientation of the diluted gases towards the circulation channel or one of the channels equipped with a bag 52.

The second assembly 8 of hydrocarbon sampling module 2 relates to the dilution air that flows into a filter 53, then into a pump 55 connected to a solenoid valve 56 and an adjustable flowmeter 54; all these elements are arranged in series on the dilution line that ends at an inlet common to several parallel channels. One of the channels only comprises a solenoid valve 57 and it is intended for passage of the dilution air before or after the sampling phase itself.

The other parallel channels, three here, comprise each a solenoid valve 58 and a sampling bag 59.

Without departing from the scope of the invention, solenoid valves 56, 57 and 58 can be replaced by any other means allowing selective orientation of the dilution air towards the circulation channel or one of the channels equipped with bags 59.

Furthermore, module 2 can comprise a system 7 for emptying and filling sampling bags 52, 59. In discharge mode, the bags are emptied from the outside air with which they were previously filled (in the filling phase). This optional procedure allows to reuse the same bags for several sampling runs.

System 7 comprises a supply line 71 delivering outside air which, in filling mode, flows through a first solenoid valve 72, a pump 73, a second solenoid valve 74, then a filter 75 that purifies the air during flushing cycles. The outside air is then split in two: one part is sent to solenoid valve 56 on the dilution air side if bags 59 need cleaning; another part of the outside air is sent to solenoid valve 29 if diluted gas sampling bags 52 need cleaning. Each solenoid valve 29, 56 controlled by a central system allows passage of the outside air or not.

In discharge mode, the air contained in the bags is discharged by following the course as follows: it passes into first solenoid valve 72, then into pump 73 and second solenoid valve 74, and it finally flows out through a specific line 76.

The assembly described above further comprises a control which controls the various solenoid valves and other active elements, so that sampling is achieved for example according to the working phase of the vehicle that discharges the exhaust gases.

Figure 3:
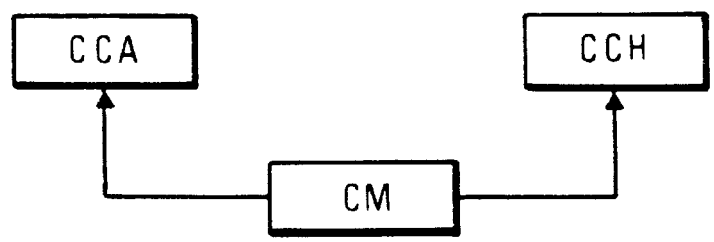
FIG. 3 is a diagram of the control unit according to the invention.

A control unit is schematically illustrated in FIG. 3. This control management unit has a programmable control device allowing to storing of all the sampling parameters during the working cycle, to ensure interactive control with the equipment of the chassis dynamometer and to activate in relation to its initial programming the various elements that make up the sampling circuits (pumps, solenoid valves . . .).

CM is the device controlling the thermal engine, with notably all the parameters characterizing a phase of its running.

CM sends suitable control signals to CCA which controls the first module 1, and signals to CCH which controls the second module 2.

It is thus possible, according to the invention, to program sampling sequences in relation to predetermined working cycles, for example in relation to standard driving cycles.

At the end of the sampling procedure, the samples stored on solid supports (such as cartridges 31, 41) or in sampling bags 52, 59 are taken to an analysis laboratory where their chromatographic analysis allows quantification of the aldehydes present both in the dilution air and the diluted gas, and hence determination of the amount of pollutants in non-diluted gases.

What is claimed is:

1. A system which samples specific pollutants contained in diluted exhaust gases from thermal combustion engines, comprising:

a first module which samples aldehyde and ketone emissions;

a second module which samples hydrocarbon emissions; and a control which coordinates the sampling performed by the first and second modules with predetermined working phases of the thermal engine; and wherein the first and second modules comprise a dilution air sampling circuit.

2. A system as claimed in claim 1, wherein first module comprises:

a circuit which traps aldehydes and ketones contained in diluted exhaust gases, comprising a gas passage simulation channel arranged parallel to at least one diluted gas sampling channel, the channels having a common inlet which receives diluted gases and a common outlet, connected to a line and comprising a filtering element, a mass flow regulator and a pump arranged in series; and wherein the dilution air sampling circuits comprise a gas passage simulation channel arranged parallel to at least one dilution air sampling channel, the channels having a common inlet which receives dilution air and a common outlet, connected to a line and comprising a filtering element, a mass flow regulator and a pump arranged in series.

3. A system as claimed in claim 2, wherein first module further comprises:

a drain circuit which cleans any circuit that has carried diluted gases and dilution air before entry into the first and second modules.

4. A system as claimed in claim 3, wherein the drain circuit comprises:

a drain gas inlet and two channels, one channel being associated with the circuit which traps aldehydes and ketones and another channel being associated with a dilution air sampling circuit, both channels opening at one end into a drain gas inlet and, another end opening into either a diluted gas inlet or a dilution air inlet.

5. A system as claimed in claim 4, wherein each channel comprises:

a solenoid valve which stops circulation in the channel, and an element which fixes a flow rate of a drain gas in the channels.

6. A system as claimed in claim 2, wherein:

the circuit which traps aldehydes and ketones comprises at least one sampling cartridge located in a sampling channel.

7. A system as claimed in claim 6, wherein:

a solenoid valve is placed downstream from each sampling cartridge, providing selective passage of the gases downstream or closing of the sampling channel downstream from the solenoid valve.

8. A system as claimed in claim 2, wherein the second module comprises:

at least one diluted exhaust gas inlet, at least a first channel equipped with a sampling bag, and a second channel, which circulates gases outside the sampling bag;

a device providing selective orientation of the exhaust gases towards one of the first and second channels;

a dilution air line, at least one channel equipped with a sampling bag and another channel which circulates dilution air outside the sampling bag; and a device which selectively orients the dilution air towards at least one of the at least one channel or the another channel.

9. A system as claimed in claim 8, wherein the second module further comprises:

a drain circuit which drains gas from at least one sampling bag contains therein by emptying/filling cycles.

10. A system as claimed in claim 9, wherein the drain circuit comprises:

a drain gas inlet, a first solenoid valve connected to a pump, a second solenoid valve, an outlet and a link circuit for connection to the at least one and the second channels.

11. A system as claimed in claim 10, wherein:

a first solenoid valve is connected to an inlet, to a pump and to a link circuit for connection to the at least one first and the second channels.

12. A system as claimed in claim 10, wherein:

the second solenoid valve is connected to an outlet, to a pump and to the link circuit for connection with the at least one first channel and the second channel.

13. A system as claimed in claim 9, wherein:

the drain circuit further comprises a filter located between the solenoid valve and two channels associated with the at least one bag, the filter purifying air during bag filling cycles.

14. A system as claimed in claim 8, wherein:

the device providing selective orientation of exhaust gas comprises a solenoid valve placed in a gas circulation channel, a solenoid valve in each channel equipped with a sampling bag and a solenoid valve upstream from the at least one first channel and the second channel.

15. A system as claimed in claim 8, wherein the device which selectively orients dilution air comprises:

a solenoid valve placed in an air circulation channel, a solenoid valve in each channel equipped with a sampling bag and a solenoid valve upstream from the at least one first channel and the second channel.

16. A system as claimed in claim 8, wherein:

the second hydrocarbon sampling module comprises two parallel channels coupled to a diluted gas inlet, one parallel channel receiving gases from diesel engines and another parallel channel receiving gases from spark-ignition engines.

17. A system as claimed in claim 16 wherein:

the channel which receives diesel exhaust gases comprises a heated filter and an element which fixes a mass flow rate of gas to be sampled.

18. A system as claimed in claim 16, wherein:

the channel which receives exhaust gases from spark-ignition engines comprises an element which fixes a mass flow rate of gas to be sampled and a contaminant filter.

19. A system as claimed in claim 16, further comprising:

a pump and a flow meter disposed upstream from the parallel channels.

20. A system as claimed in claim 8, wherein the dilution air line comprises:

a filter, a pump and an adjustable flowmeter disposed upstream from the at least one first channel and the second channel.

* * * * *